United States Patent [19]

Luukkala et al.

[11] Patent Number: 4,551,030
[45] Date of Patent: Nov. 5, 1985

[54] PROCEDURE AND MEANS FOR EXAMINING THE SURFACE QUALITY OF MATERIALS IN SOLID STATE

[76] Inventors: Mauri Luukkala, Haukilahdenranta 23 B 5, 02170 Espoo 17; Ari Lehto, Raekuja 3, 00700 Helsinki 70, both of Finland

[21] Appl. No.: 557,174
[22] PCT Filed: Mar. 14, 1983
[86] PCT No.: PCT/FI83/00023
 § 371 Date: Nov. 3, 1983
 § 102(e) Date: Nov. 3, 1983
[87] PCT Pub. No.: WO83/03303
 PCT Pub. Date: Sep. 29, 1983

[30] Foreign Application Priority Data

Mar. 15, 1982 [FI] Finland ............................ 820884

[51] Int. Cl.$^4$ .................................... G01N 25/72
[52] U.S. Cl. ............................ 374/5; 374/7; 374/129; 250/338; 356/237
[58] Field of Search ................ 374/129, 4, 5, 7, 43

[56] References Cited

U.S. PATENT DOCUMENTS

| | | | |
|---|---|---|---|
| 3,043,956 | 7/1962 | Cohen | 250/83.3 |
| 3,222,917 | 1/1965 | Roth | 374/5 |
| 4,255,971 | 3/1981 | Rosencwaig | 73/606 |
| 4,430,897 | 2/1984 | Quate | 374/5 |
| 4,513,384 | 4/1985 | Rosencwaig | 374/7 |

FOREIGN PATENT DOCUMENTS 2502289 3/1975 Fed. Rep. of Germany .
WO81/03704 12/1981 PCT Int'l Appl. .
1403950 8/1975 United Kingdom .

OTHER PUBLICATIONS

"Thermal Wave Electron Microscopy of Metals", A. Rosencwaig, Sep. 8, 1980, Thin Solid Films, 77 (1981) pp. L43–L47.
"Alternating Beam Method in Photothermal Microscopy and Photoacoustic Microscopy", A. Lehto et al, Electronics Letters, Jul. 23, 1981, vol. 17, No. 15, pp. 540–541.

Primary Examiner—Charles Frankfort
Assistant Examiner—Thomas B. Will
Attorney, Agent, or Firm—Steinberg & Raskin

[57] ABSTRACT

The characteristics of various solid materials, in particular, surfaces of and coatings on metals and thickness of surface hardening layers are measured without damaging the specimen. The phase angle of a continuous thermal surface wave produced by a modulated light beam is measured. The phase angle of the continuous thermal wave progressing along the surface of the specimen is measured by temperature detectors either at a fixed distance from the light spot, as a function of frequency, or at a fixed frequency, as a function of distance. The phase angle of the thermal wave depends upon the thickness of the surface hardened layer whereby such thickness is measured.

15 Claims, 4 Drawing Figures

PROCEDURE AND MEANS FOR EXAMINING THE SURFACE QUALITY OF MATERIALS IN SOLID STATE

The present invention relates to a procedure and means for examining the surface qualities of materials in solid state. More particularly, the invention relates to a procedure and means for examining surface qualities and defects of solid state materials such as metals, or the equivalent, and the properties of their coatings, such as adhesion. This is accomplished by using a light beam and without destruction of the material. The procedure and means may also be used for measuring other types of coating, such as, for example, plasma coatings. In the interest of perspicuity, however, the following disclosure is concentrated specifically on coatings on metals and particularly on surface hardening.

Examination of coatings and of the surface hardening of steel is usually carried out by cutting a piece from the object to be examined and examining the structure of the surface, or the thickness of the coating, from one side with an optical microscope. If it is desired to examine the distribution of hardness in the surface, the usual procedure is to press a pointed diamond stylus into the surface of the specimen with constant force and to measure the depth of the resulting depression. The greater the hardness, the shallower the depression. This type of instrument is called a Vickers hardness tester. Similarly, it is also possible to measure the thickness and other characteristics of paint coat, for example, from the side. In case the object to be examined is precious, it is most awkward to cut off specimens.

SUMMARY OF THE INVENTION

The principal object of the invention is to measure the surface characteristics of solid materials without contacting the specimen.

An object of the invention is to measure the thickness of a surface-hardened layer of steel without contacting the specimen.

Another object of the invention is to provide a device and procedure for measuring the surface characteristics of solid material without contacting the specimen.

Still another object of the invention is to provide a device and procedure for measuring the surface characteristics of solid material which provides accurate measurements.

Yet another object of the invention is to provide a device and procedure for measuring the surface characteristics of solid state material with accuracy, facility and ease.

The objects of the invention are achieved, for example, by making use of the so-called photothermic effect. If a light beam is directed on the surface of a specimen, part of the light energy is absorbed by the specimen surface and converted into heat. If the light is intensity-modulated at a given frequency, the heating will also be periodic with the same frequency. If the intensity of the incident light is represented by the equation $I = I_o/2 (1 + \cos \omega t)$, where $I_o/2 \cos \omega t$ represents the alternating component of the light intensity, then also the temperature at the light spot conforms to the equation $$T = (T_o/2)(1 + A(\omega) \cdot \cos(\omega t + \phi)).$$

Here, $T_o/2$ represents the static rise of temperature on the surface and $T_o/2\, A(\omega) \cos(\omega t + \phi)$, the alternating component, which displays a certain phase shift $\phi$ with reference to the light. $A(\omega)$ is the amplitude factor of the temperature, dependent on frequency. This periodic heating of the surface is propagated along the surface of the specimen, and into it, as a kind of "heat wave" or "thermal wave". This thermal has a given wavelength and phase angle, the phase changing as a function of time and location. The depth of penetration of the thermal wave is the so-called thermal diffusion length $$\mu = \sqrt{\frac{2\alpha}{\omega}},$$

wherein $\omega$ the angular frequency of modulation of the light and $\alpha$ is the thermal diffusivity of the material in question. The penetration of the thermal wave into the material may be expressed by the equation $$T = T_o e^{-\sqrt{\frac{\omega}{2\alpha}} \cdot x} \sin(\omega t - \sqrt{\frac{\omega}{2\alpha}} \cdot x)$$

where x is the distance which the wave has travelled. It is seen that the thermal wave is exponentially attenuated and the associated phase angle $\phi$ has the form $$\phi = \sqrt{\frac{\omega}{2\alpha}} \cdot x$$

It is important to observe that although the thermal wave penetrates into the material, part of it still proceeds along the surface of the object in the plane of the surface. In the procedure of the invention, the continuous thermal wave propagated along the surface and its phase angle is measured as a function of location x or as a function of $\omega$ with an infra-red detector or a thermocouple. This is done because it can be shown that the wave progressing along the surface is quite sensitive specifically to the properties of the surface and to the quality of various coatings.

It is highly important to note that the phase difference is measured at least at two different values of x or at least at two different values of $\omega$. This enables the fixed phase differences present in the apparatus to be eliminated and the true thermal diffusivity of the surface to be estimated. In any other procedure an incorrect value would be obtained for the thermal diffusivity. The present invention differs in this respect from all apparatus and procedures known in the art.

The procedure and apparatus of Finnish patent application No. 801850 uses a light source, or laser, modulated at a given frequency and an infra-red meter recording the periodic increase of the surface temperature. This apparatus operates well enough in itself and performs various types of measurements on coatings. It has been found, however, that the sensitivity of this apparatus is fairly low, particularly in surface hardening measurements. In the apparatus of the Finnish patent application No. 801850, the periodic variation of surface temperature is observed over a comparatively extensive area. Because the periodic temperature increase is highest specifically at the point where the laser beam strikes the surface, the apparatus will measure the properties of the specimen surface mainly at the location of the light spot only. In the present invention, the amplitude and phase angle of the thermal wave are specifically measured at a great enough distance from the point heated by the light. When the phase angle of the continuous thermal wave progressing close to the surface is measured or along the surface, it is naturally most sensitive exactly to the properties of the surface. Since it is possible to measure the phase angle without contact with an infra-red detector, no load whatsoever is imposed on the propagation characteristics of the thermal surface wave. It is possible at the same time to measure the behavior of the phase angle as a function of distance x by displacing the detector gradually away from the heating light spot. If the diffusivity of the specimen surface is $\alpha_p$, the phase angle $\phi$ of the thermal wave progressing along the surface at a given frequency $\omega$ is also determined by the equation $$\phi = \sqrt{\frac{\omega}{2\alpha_p}} \cdot x$$

If the contactless infra-red detector is connected to a phase detector, where the phase of the measured signal is compared with a fixed reference signal having the same frequency $\omega$, it is easy to calculate the diffusivity $\alpha_p$ of the surface from the output of the phase detector, because x is known. The diffusivity $\alpha_p$ is dependent upon the quality of the coating, and in the case of surface hardening, for example, it is dependent upon the thickness of the surface-hardened layer. It is likewise possible to estimate the thickness and adhesivity of paint coats or of so-called plasma layers, for example.

The procedure and apparatus of the invention have the further advantage that since the angular frequency of modulation $\omega$ can be regulated, it is possible at the same time to control the depth of penetration of the thermal wave and thereby the accuracy of measurement in the case of thin coatings. Two different techniques for measuring diffusivity can be applied with the practical measuring apparatus. In the first, the measuring distance x from the light spot is kept constant and is adjusted. In the second, $\omega$ is kept constant and the phase angle is measured for several different values of x. It is believed that the second mode is easier to carry out in practice.

Another special feature of the present invention is that the phase angle of the thermal wave progressing along the surface is measured by means of temperature pick-ups where the metallic specimen itself constitutes a component of the thermocouple. It is known from basic physics that if a junction is formed of two different metals and this junction is heated, an electromotive force builds up across the junction which is dependent on the temperature. In the present invention, the tip of a tungsten wire, for example, is pressed against the surface of the metallic specimen and the voltage produced between the specimen and the tungsten wire is measured by an electronic measuring instrument. When heating up, the specimen forms a thermocouple with the tip of the tungsten wire and the thermal load caused by the wire will be minimal. It is thus possible to change the distance x between the light spot and the measuring tip with reference to each other by moving said light spot and said tip with reference to each other, to determine the phase angle of the thermal surface wave in the manner hereinbefore described.

In another arrangement, two closely spaced metal tips are pressed against the specimen. The metal tips consist of such metal that they form a thermocouple with the specimen itself. The advantage of this arrangement is that no particular electrical contact need be provided with the specimen for measuring the generated voltage. Instead, the voltage between the two tips constituting the thermocouple is measured. If the tips are spaced by a given, appropriate distance, the phase angle of the thermal surface wave is immediately obtained from the phase difference between the voltages produced by these two thermocouples.

The aforedescribed arrangement has the advantage that the set-up is not highly critical as regards the quality of contact between the tip and the specimen, since in the measurement specifically the phase angle is observed, which is independent of the amplitude of the electrical signal itself. On the other hand, the aforedescribed arrangement is independent of variations which may occur in the ambient lighting and of diffuse light scattered by the specimen surface. Thirdly, the specimen itself serves as one component of the thermoelectric couple, whereby no thermal loading effect imposed on the surface by a conventional thermocouple to be mounted separately is incurred.

In experiments carried out in practice, much stronger signals have been obtained with this thermocouple arrangement than with infra-red detectors, the sensitivity to interference being reduced at the same time. It is to be noted, on the other hand, that infra-red detectors may be used to measure the properties of insulating materials as well.

U.S. Pat. No. 3,222,917 discloses that defects, cracks, etc. may be measured in objects, since a single local thermal pulse is produced in the specimen. This thermal pulse is then detected by thermocouples or the equivalent, for example, pressed against the surface. It is then possible, by observing the time of ascent, the time of descent and the shape of the heat pulse derived from these thermocouples, to draw conclusions concerning the properties of the specimen. The present invention does not employ a single pulse and its deformation; it uses continuously intensity-modulated light as the source of a continuous thermal wave and measures the behavior of the phase angle of such continuous wave. Furthermore, no phase angle can be defined for a single pulse. The phase angle is exclusively a characteristic of a continuous wave. Another decisively important difference is that since the modulation frequency $\omega$ can be controlled, it is also possible to control the depth of penetration of the thermal wave. The single-pulse arrangement does not afford this possibility. Since we are interested in coatings, we have to be able to control the depth of penetration by means of an appropriate $\omega$, because it should be remembered that the depth of penetration is inversely proportional to the square root of $\omega$. It should further be noted that if temperature pick-ups are pressed against the surface, they may alter the propagation of the thermal pulse on the surface. This is why the apparatus of the present invention uses contactless infra-red meters or a thermocouple where the specimen itself is a component of the thermocouple.

U.S. Pat. No. 3,043,956 discloses an arrangement wherein the specimen is irradiated by a modulated infra-red source and is then observed with the aid of infra-red detectors, and the phase of the resulting signal is observed with reference to the phase of the modulation of the radiation source. In the present invention, firstly, no infra-red light source is used like in said U.S. patent. Secondly, in the present invention, the wave progressing along the surface is specifically studied, and its phase is studied as a function of the distance travelled across the surface. The measurement itself is made specifically at a point different from that on which the incident light or radiation is directed, and the use of the aforedescribed distance x as a parameter is essentially important with a view to measuring the quality of the coating and the thermal diffusivity of the surface. The U.S. patent discloses an arrangement wherein the infra-red source and the detector are mounted on one and the same side of the specimen with a given mutual spacing, but this arrangement is chosen in order to compensate for the movement of the specimen. This arrangement also fails to vary the distance x in the direction of the surface for measurement of phase differences.

BRIEF DESCRIPTION OF THE DRAWINGS

For a fuller understanding of the invention, reference is had to the following description, taken in connection with the accompanying drawings, in which.

DESCRIPTION OF PREFERRED EMBODIMENTS

Figure 1:
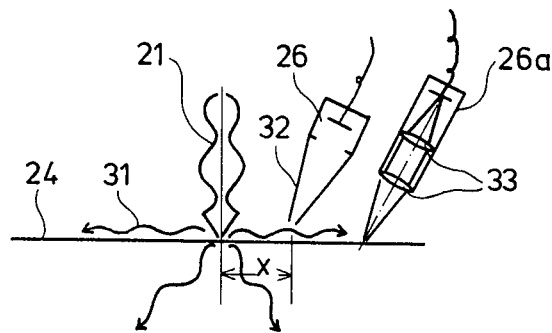
FIG. 1 is a schematic illustration of the generation and propagation of the thermal surface wave by the apparatus of the invention.

As shown in FIG. 1, a light beam 21, intensity-modulated at a given frequency, periodically heats a desired point on the surface of the specimen 24. The heated point emits a thermal wave 31 in all directions in the specimen 24, and part of the thermal energy proceeds as a wave 31 along the surface of said specimen with a given velocity and a given phase angle, dependent on location and on the thermal diffusivity of said surface. The wave 31, proceeding along the surface is observed by one or several infra-red detectors 26, 26a mounted in a suitable manner. The aperture of the infra-red detector is limited so that it monitors only a small part of the specimen's surface whereby the direct thermal radiation of the scattered visible light radiation from the illuminated point does not strike the detector. The aperture may be limited by a trumpet-like structure 32 or an infra-red lens assembly 33, for example. The measuring distance of the infra-red detector from the illuminated point can be adjusted in the direction of the surface by mechanical arrangements, for example. Furthermore, the detector is AC-connected. In other words, the detector only observes the alternating signal, but not the static temperature rise in the specimen.

Figure 2:
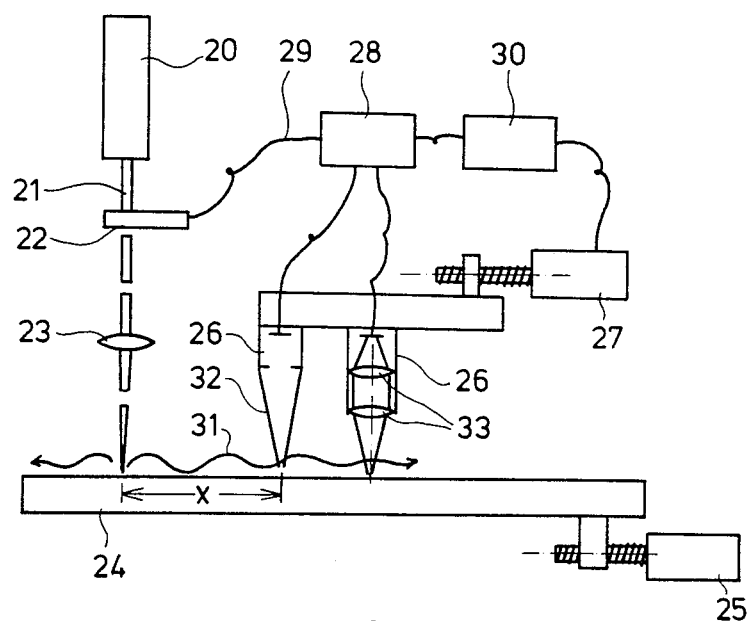
FIG. 2 is a block diagram of an embodiment of the apparatus of the invention.

FIG. 2 schematically depicts the apparatus as a whole. The light beam 21 coming from the light source 20, which is usually a laser, passes through a light intensity modulator 22 operating at an adjustable frequency, to the focusing lens 23, the specimen 24 being mounted in the focal plane of said lens. If desired, the specimen may be moved in the focal plane by an electrically controlled specimen positioner 25. The thermal surface wave 31 emitted by the specimen surface heated by the light beam 21 is observed by one or several infra-red detectors 26 mounted far enough from the light spot. The aperture of each detector is limited in a convenient way so that it monitors only a small enough part of the specimen surface. The distance of the infra-red detector from the light spot in the direction of the surface can be controlled as desired by an electrical detector positioner 27. The signal from the infra-red detectors 26 is conducted to a phase-sensitive or phase detector 28. A fixed reference signal 29 from the light modulator 22 is simultaneously supplied to the phase-sensitive detector 28. The output signal from the phase-sensitive detector 28 is fed to a suitable output device 30, which may be a recorder or a microprocessor, for example. The microprocessor may control the detector positioner 27 so that an output record of the phase angle is obtained as a function of the distance x. It is obvious that if the specimen surface is heated at one single point, the thermal wave on the surface of the specimen 24 will start to progress radially. The aperture of the infra-red detector may then be limited by a trumpet structure shaped like a half-circle, for example. If the heating is in band fashion, for example, the aperture may consist of a slit-like trumpet structure. A slit-like aperture may also be provided by a cylindrical lens, which should be germanium, which is transparent to infra-red rays.

Figure 3:
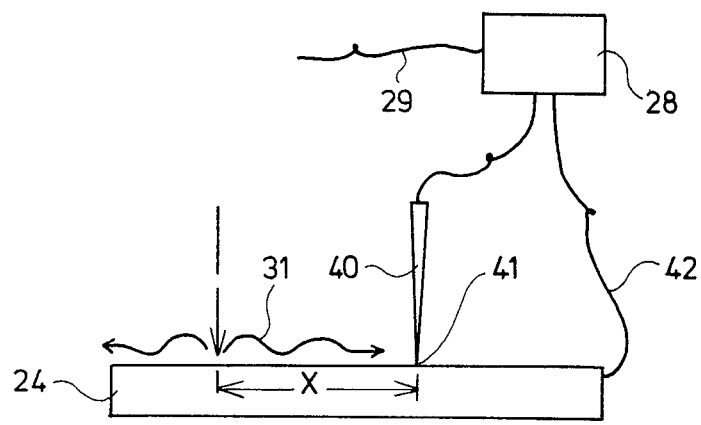
FIG. 3 is a schematic diagram of another embodiment of the apparatus of the invention for measuring phase differences with the aid of metallic points.

FIG. 3 shows measuring apparatus in which the metallic specimen itself is part of a thermocouple. The phase angle of the thermal surface wave 31 progressing along the surface of the metallic specimen 24 is measured by a metallic measuring point 40 pressed against the surface. The material of the point 40 is so selected that the junction 41 with the metallic specimen constitutes a thermocouple. The electromotive force, dependent on temperature and generated in this thermocouple, is measured with the phase-sensitive detector 28 as a function of the distance x between the light spot and the measuring point with at least two different values of x. In order to accomplish a closed circuit, the specimen 24 has to be connected to the detector 28 by a lead 42. It is also necessary to conduct a reference signal from the light modulator to the phase-sensitive detector 28, in accordance with the well-known principles of phase measurement. The distance x is controlled in the same manner as in the arrangement shown in FIG. 2.

Figure 4:
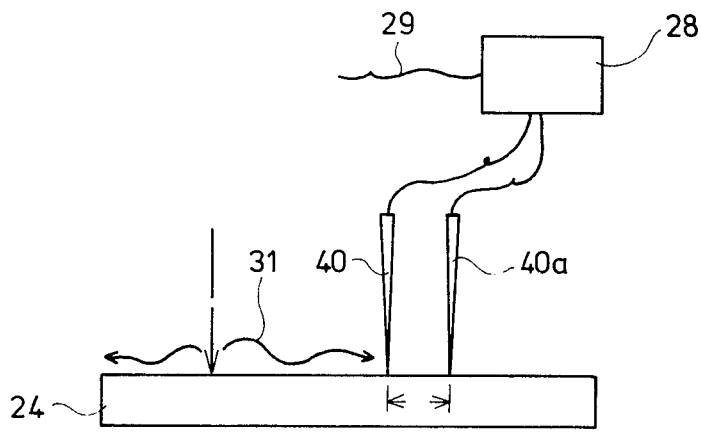
FIG. 4 is a schematic diagram of still another embodiment of the apparatus of the invention for measuring phase differences with the aid of two points.

FIG. 4 shows an arrangement in which the phase difference is measured by using two measuring points 40 and 40a, with the metallic specimen 24 being part of the thermocouple in them. A closed circuit is established through both measuring points 40 and 40a, whereby no separate lead is required as in the embodiment of FIG. 3. Since the measurement occurs at two different points, it is not absolutely necessary to adjust the distance between the light spot and the points of measurement, and one single measurement is sufficient to elicit the correct phase difference.

The materials of the measuring points have to be of such substance that a thermoelectric voltage is generated between the measuring point and the metallic specimen. It has been established by experiments that a measuring point made of tungsten, for example, yields a good signal. Also, measuring points made of sintered materials produce excellent signals.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A procedure for measuring thermal diffusivity of solid materials, such as metals, coatings and surface layers and thickness and other characteristics of a surface hardening layer, said procedure comprising the steps of
   illuminating a surface of a body under examination by an intensity-modulated light beam at a desired frequency to produce a continuous, progressing thermal wave having a phase angle;
   measuring the phase angle of said wave in the direction of said surface at a distance from a spot at which said light beam illuminates said surface of said specimen; and
   comparing the measured phase angle with a fixed phase reference signal to produce an output signal determined by said phase angle and thereby indicative of the thickness of the surface hardened layer of said specimen.

2. A procedure as claimed in claim 1, wherein said phase angle is measured as a function of the distance from said spot in the direction of said surface.

3. A procedure as claimed in claim 1, wherein said phase angle is measured as a function of the modulation frequency of said light beam.

4. A procedure for measuring thickness and other characteristics of solid materials, such as coatings on and surface layers of metals and surface hardening layers, said procedure comprising the steps of
   producing a light beam and directing said light beam to a surface of a specimen under examination;
   modulating said light beam in intensity at a desired frequency;
   detecting temperature at the surface of said specimen, said light beam heating the surface of said specimen periodically so that a continuous and progressing thermal wave is produced at said surface of said specimen, said wave having a phase angle measured as a function of the distance from a spot at which said light beam illuminates said surface of said specimen in the direction of said surface;
   detecting the phase of detected temperatures; and
   deriving a reference signal having a fixed phase from the light modulation and comparing it with the detected phases thereby producing an output signal determined by said phase angle and thereby indicative of the thickness of the surface hardened layer of said specimen.

5. A procedure as claimed in claim 4, wherein said temperature is detected at a space from said specimen whereby the distance of a point of measurement from said spot in the direction of said surface is constant, but the phase angle of said wave is measured as a function of the frequency of the light intensity modulation.

6. Apparatus for measuring thickness and other characteristics of solid materials, such as coatings on and surface layers of metals and surface hardening layers, said apparatus comprising
   a light source for producing a light beam and directing said light beam to a surface of a specimen under examination;
   light intensity modulating means interposed in said light beam for modulating said light beam at a desired frequency;
   temperature detecting means in operative proximity with the surface of said specimen, said light beam heating the surface of said specimen periodically so that a continuous and progressing thermal wave is produced at said surface of said specimen, said wave having a phase angle measured as a function of the distance of said temperature detecting means from a spot at which said light beam illuminates said surface of said specimen in the direction of said surface;
   a phase detector connected to said temperature detecting means; and
   a reference signal source connected to said phase detector and supplying to said phase detector a reference signal having a fixed phase from said light intensity modulating means, said phase detector receiving an output signal from said temperature detecting means and producing an output signal determined by said phase angle and thereby indicative of the thickness of the surface hardened layer of said specimen.

7. Apparatus as claimed in claim 6, wherein said temperature detecting means comprise infra-red detector means.

8. Apparatus as claimed in claim 6, wherein said temperature detecting means comprise infra-red detectors spaced from said surface of said specimen whereby the distance of a point of measurement from said spot in the direction of said surface is constant, by the phase of said wave is measured as a function of the frequency of the light intensity modulation.

9. Apparatus as claimed in claim 8, wherein each of said infra-red detectors has a measuring aperture limited in size so that each of said infra-red detectors detects a small part of said surface of said specimen.

10. Apparatus as claimed in claim 9, further comprising focusing lens means intercepting said light beam for providing a determined shape of said spot, and wherein said measuring aperture is limited in size by a trumpet-like structure having an aperture of substantially the same shape as said spot.

11. Apparatus as claimed in claim 9, further comprising focusing lens means intercepting said light beam for providing a predetermined shape of said spot, and wherein said measuring aperture is limited in size by infra-red lens means which produces an aperture of substantially the same shape as said spot.

12. Apparatus for measuring thickness and other characteristics of solid materials, such as coatings on and surface layers of metals and surface hardening layers, said apparatus comprising
   a light source for producing a light beam and directing said light beam to a surface of a specimen under examination;
   light intensity modulating means interposed in said light beam for modulating said light beam at a desired frequency, said light beam heating the surface of said specimen periodically so that a continuous and progressing thermal wave is produced at said specimen;
   measuring means in thermal and electrical contact with said surface of said specimen, said measuring means constituting a thermoelectric couple with said specimen, said wave having a phase angle measured as a function of the distance in the direction of said surface of said measuring means;

phase detecting means connected to said measuring means; and reference signal means connected to said phase detecting means and supplying to said phase detecting means a reference signal having a fixed phase from said light intensity modulating means, said phase detecting means receiving an output signal from said measuring means and producing an output signal determined by said phase angle and thereby indicative of the thickness of the surface hardened layer of said specimen.

13. Apparatus as claimed in claim 12, wherein said measuring means comprises a measuring point.

14. Apparatus as claimed in claim 12, wherein said measuring means comprises measuring points.

15. Apparatus as claimed in claim 12, wherein said measuring means measures said phase angle of said wave and comprises a pair of measuring points contacting said surface of said specimen in spaced relation from with a spot at which said light beam illuminates said surface of said specimen and in spaced relation with each other so that said measuring points are at different distances from said spot and electrically connected in a manner whereby they form a circuit with said specimen.

* * * * *